United States Patent [19]

McKee

[11] Patent Number: 5,012,672
[45] Date of Patent: May 7, 1991

[54] HYDROGEN GAS SENSOR AND METHOD OF MANUFACTURE

[75] Inventor: John M. McKee, Hinsdale, Ill.

[73] Assignee: The United States of America as represented by the United States Department of Energy, Washington, D.C.

[21] Appl. No.: 382,199

[22] Filed: Jul. 17, 1989

Related U.S. Application Data

[62] Division of Ser. No. 93,378, Sep. 3, 1987, abandoned.

[51] Int. Cl.$^5$ .............................................. G01N 37/00
[52] U.S. Cl. .................................. 73/31.07; 73/19.12; 29/455.1
[58] Field of Search ............................ 73/19; 29/455.1

[56] References Cited

U.S. PATENT DOCUMENTS

| | | |
|---|---|---|
| 2,671,336 | 3/1954 | Hulsberg . |
| 2,671,337 | 3/1954 | Hulsberg . |
| 3,060,726 | 10/1962 | Weber . |
| 3,104,960 | 9/1963 | Chamerlin et al. . |
| 3,279,241 | 10/1966 | Pement . |
| 3,681,026 | 8/1972 | Holden . |
| 3,683,272 | 8/1972 | Vissers et al. . |
| 3,731,523 | 5/1973 | Vissers et al. . |
| 3,886,444 | 5/1975 | Roy et al. . |
| 3,949,593 | 4/1976 | Oertle . |
| 3,977,232 | 8/1976 | Hickam et al. . |
| 4,003,725 | 1/1977 | Bunn, Jr. et al. . |
| 4,092,844 | 6/1978 | Oertle et al. . |
| 4,143,316 | 3/1979 | Roy et al. . |
| 4,331,023 | 5/1982 | Allersma et al. . |
| 4,461,165 | 7/1984 | Kesson . |

FOREIGN PATENT DOCUMENTS 684865 12/1952 United Kingdom .

Primary Examiner—Hezron E. Williams
Assistant Examiner—Joseph W. Roskos
Attorney, Agent, or Firm—Tyrone Davis; Robert J. Fisher; William R. Moser

[57] ABSTRACT

A sensor for measuring the pressure of hydrogen gas in a nuclear reactor, and method of manufacturing the same. The sensor comprises an elongated tube of hydrogen permeable material which is connected to a pressure transducer through a feedthrough tube which passes through a wall at the boundary of the region in which hydrogen is present. The tube is pressurized and flushed with hydrogen gas at an elevated temperature during the manufacture of the sensor in order to remove all gasses other than hydrogen from the device.

14 Claims, 1 Drawing Sheet

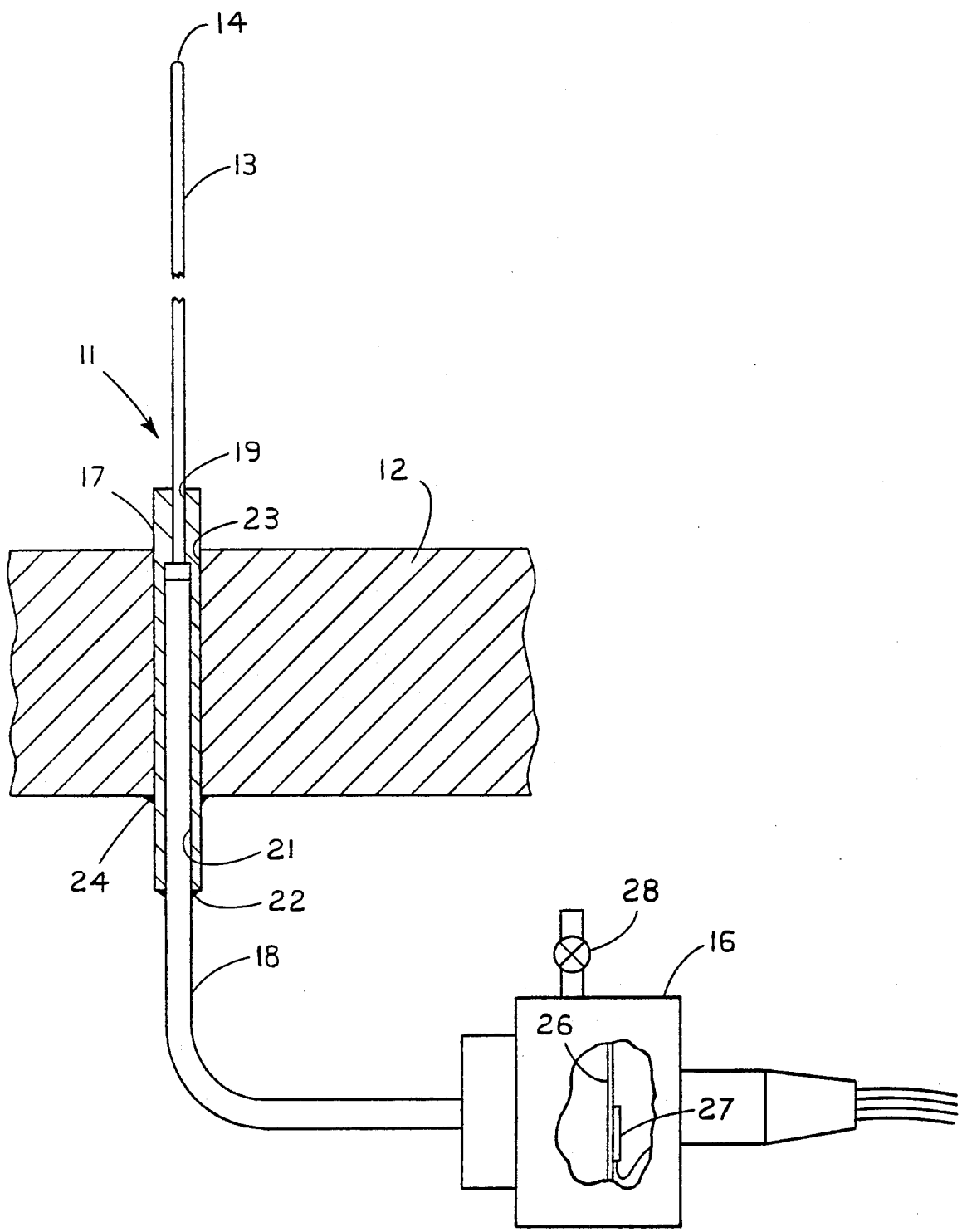

HYDROGEN GAS SENSOR AND METHOD OF MANUFACTURE

This invention was made in the course of, or under Contract No. W31-109-Eng-38 with the United States Government as represented by the United States Department of Energy, and the government has certain rights in the invention.

This is a division, of application Ser. No. 07/093,378 filed Sept. 3, 1987, now abandoned.

This application pertains generally to the measurement of gas pressure, and more particularly to a hydrogen gas sensor suitable for use in nuclear reactors and to a method of manufacturing the same This invention was made with the Government support under the Participation Agreement between the Department of Energy and the Electric Power Research Institute exercised pursuant to Prime Contract No. W-31-109-ENG-38 between the Department and the University of Chicago, Operator of Argonne National Laboratory. The Government has certain rights in this invention.

In nuclear reactors, there is frequently a need to detect the presence of hydrogen gas which can burn or even explode if not properly contained. Some meltdown tests have, for example, been conducted on fuel pins having a zirconium cladding which melts at temperatures in the range of 3000° F. Such tests are generally conducted in a steam atmosphere, with fission heating to produce the high temperatures. At these temperatures, the zirconium reacts with the steam to form zirconium oxide and hydrogen gas. Depending upon the pressure of the steam, the hydrogen thus produced typically has a partial pressure on the order of 50-500 psi. To prevent fires or explosions, this gas must be carefully confined.

Measuring the amount and rate of hydrogen generation during such tests is difficult because of the high pressure and high temperature involved and because of the radioactive environment in which the measurement must be made. Also, the measurement must be made quickly since the hydrogen generation period may be as short as 1-2 minutes. In addition, the space available for hydrogen monitoring equipment may be limited, and there may also be limitations on the allowable penetrations of the containment structure.

U.S. Pat. Nos. 2,671,336 and 2,671,337 disclose hydrogen sensors utilizing hydrogen permeable members for measuring the concentration of hydrogen in the presence of other gasses. U.S. Pat. No. 3,060,726 discloses a sensor for monitoring the hydrogen concentration of a liquid in a pressurized vessel. U.S. Pat. Nos. 3,683,272 and 3,731,523 disclose devices for measuring hydrogen concentration in liquid sodium systems, and U.S. Pat. No. 3,683,272 shows the use of an absorbtion vacuum pump to provide an initial vacuum. U.S. Pat. No. 3,681,026 describes a method and apparatus for measuring carbon activity in which a vacuum pump is coupled to a hydrogen permeable bulb for removing hydrogen from the system. Each of these devices has certain limitations and disadvantages.

It is in general an object of the invention to provide a new and improved hydrogen gas sensor and method of manufacturing the same.

Another object of the invention is to provide a hydrogen sensor and method of the above character which overcome the limitations and disadvantages of hydrogen sensors heretofore provided.

Another object of the invention is to provide a hydrogen sensor and method of the above character in which the sensor is capable of measuring hydrogen at high temperatures and pressures ranging from less than one to hundreds of atmospheres in the presence of fission products and steam.

Another object of the invention is to provide a hydrogen sensor and method of the above character in which a sensor is suitable for use in nuclear reactors and other enclosures in which hydrogen may accumulate.

These and other objects are achieved in the invention by connecting a pressure transducer to one end of an elongated tube of hydrogen permeable material which is sealed at the other end, exposing the tube to pressurized hydrogen gas at an elevated temperature and allowing the hydrogen gas to diffuse through the wall of the tube and flow through the tube and out through a vent opening in the transducer for a time sufficient to remove all other gasses from the tube, closing the vent opening to seal the tube and trap some of the hydrogen gas in the tube, and cooling the tube so that the hydrogen trapped in the tube diffuses out through the wall of the tube to form a vacuum within the tube.

The single FIGURE of drawing is a somewhat schematic illustration of one embodiment of a hydrogen gas sensor according to the invention.

In the drawing, the hydrogen sensor 11 is illustrated in conjunction with the wall 12 at the boundary of a pressurized area. Wall 12 might, for example, be the wall of a containment vessel, or it might be part of a test vehicle which operates within a reactor.

The sensor includes an elongated tube 13 fabricated of a material which is highly permeable to hydrogen but substantially impervious to all other gasses. In one presently preferred embodiment, the tube is fabricated of a palladium-silver alloy containing on the order of 75% palladium and 25% silver. The tube preferably has a small outer diameter (e.g., 1/16 inch) in order to withstand high external pressure without collapsing and to minimize the amount of hydrogen that must diffuse through the wall of the tube. The tube has a relatively thin wall (e.g., 0.010 inch) to provide rapid hydrogen permeation and fast response time. The tube is relatively long (e.g., 60 inches) to provide a relatively large membrane area and to minimize the time required to supply hydrogen to a transducer connected to the tube. The arrangement of the tubing is not critical, and the tube can be arranged in any convenient manner, such as a helical coil.

The inner end of sensor tube 13 is welded shut, as indicated by reference numeral 14. The outer end of the sensor tube is connected to a pressure transducer 16 by means of a feedthrough tube 17 and an output tube 18. The feedthrough tube is fabricated of a material such as nickel, and the outer end of sensor tube 13 is received in an axial bore 19 at the inner end of the feedthrough tube. The joint between the sensor tube and the feedthrough tube is sealed by brazing with a suitable material such as a gold-nickel alloy containing 82% gold and 18% nickel.

One end of tube 18 is received in an axial bore 21 at the outer end of feedthrough tube 17 so that the passageways in tubes 13 and 17 are aligned axially and in direct communication with each other. Tube 18 is fabricated of a material such as stainless steel which is not permeable to hydrogen, and it is sealed to feedthrough tube 17 by a fillet weld 22 at the outer end of the feedthrough tube.

Feedthrough tube 17 extends through a bore 23 in wall 12 and is sealed to the wall by a fillet weld 24 at the outer end of the bore.

The diameter of feedthrough tube 17 is only slightly greater than the diameter of sensor tube 13. In one presently preferred embodiment, the sensor tube as an outer diameter of 1/16 inch, and the feedthrough tube has an outer diameter of ¼ inch. In this embodiment, output tube 18 has an outer diameter of ⅛ inch and an inner diameter of 0.025 inch.

Pressure transducer 16 has a pressure responsive diaphragm 26 which is exposed to the interior of sensor tube 13 through feedthrough tube 17 and output tube 18. This diaphragm is fabricated of a material such as stainless steel which is not permeable to hydrogen gas, and deformation of the diaphragm is monitored by strain gauges 27 mounted on the backside of the diaphragm. The strain gauges thus produce electrical signals corresponding to the pressure within sensor tube 13. The pressure transducer housing is constructed so that the total internal volume of the output tube 18 and pressure transducer 16 is small, typically less than the internal volume of the sensor tube 13.

The transducer also has a small bleed valve 28 which can be opened to release gasses from the sensor assembly.

Gasses other than hydrogen are removed from inside the sensor tube and the pressure transducer. This is done by heating the sensor tube to a temperature on the order of 700° F. and exposing the exterior of the tube to pressurized hydrogen gas With valve 28 open. The hydrogen diffuses through the wall of the sensor tube and flows rapidly through the passageway or chamber within the tube to the transducer and out through the open bleed valve. The flow rate of the hydrogen from the bleed valve can be monitored with a flow meter to confirm the permeability of the wall or membrane of the sensor tube. The hot hydrogen is allowed to flow for an extended period of time, e.g., an hour or more, in order to make certain that all other adsorbed gasses are removed from the interior surfaces of the device.

Once the gasses have been removed, the bleed valve is closed, sealing the sensor tube with some of the hot hydrogen trapped therein. The external pressurization of the tube is discontinued, and as the tube cools, the hydrogen within the tube diffuses out of the tube, forming a vacuum within the tube. This vacuum is measured with the pressure transducer and monitored for an extended period of time (e.g., 12 hours or more) to assure that a leak-tight system has been achieved. Thereafter, when the sensor tube is exposed to hydrogen gas, the hydrogen diffuses into the tube, and its presence and pressure are detected and monitored by the pressure transducer.

The invention has a number of important features and advantages. Although decreasing temperatures and minor surface contamination may reduce the permeability of the sensor tube to hydrogen, this only slows down the rate at which the final equilibrium pressure is reached. It does not change that pressure. Thus, an accurate measurement is obtained even though there is no control of the membrane temperature and even though there may be some contamination of the membrane.

The materials which are exposed to the reactor environment are all metallic and highly resistant to corrosion and radiation. They are strong, ductile, and have high melting points. Thus, the sensor has a high integrity and a high reliability.

It is apparent from the foregoing that a new and improved hydrogen sensor and method of manufacturing the same have been provided. While only certain presently preferred embodiments have been described in detail, as will be apparent to those familiar with the art, certain changes and modifications can be made without departing from the scope of the invention as defined b the following claims.

I claim:

1. In a method of manufacturing a sensor for monitoring the pressure of hydrogen gas, the steps of: sealing one end of an elongated tube having a hydrogen permeable wall defining an internal chamber, connecting the other end of the tube to a pressure transducer with the chamber in communication with a pressure responsive element in the transducer, providing a vent opening in the transducer, exposing the exterior of the tube to pressurized hydrogen gas at an elevated temperature and allowing the hydrogen gas to diffuse through the wall of the tube into the chamber and to flow out through the vent opening for a time sufficient to remove all other gasses from the chamber, closing the vent opening to seal the chamber with some of the hydrogen gas trapped therein, and cooling the tube so that the hydrogen gas trapped in the chamber diffuses out through the wall of the tube to form a vacuum in the chamber.

2. The method of claim 1 wherein the tube is at a temperature on the order of 700° F. during the time the pressurized hydrogen gas is diffusing into the chamber.

3. The method of claim 1 wherein the hydrogen gas is allowed to flow through the chamber for a time on the order of one hour.

4. The method of claim 1 wherein the elongated tube is connected to the pressure transducer by a feedthrough tube, and the method further includes the steps of positioning the feedthrough tube in an opening in a boundary wall of the region where the pressure of hydrogen gas is to be measured with the elongated tube extending into the region and the pressure transducer being positioned outside the region, and forming a seal between the feedthrough tube and the boundary wall.

5. The sensor manufactured by the method as recited in claim 4, wherein said tube is fabricated of a palladium-silver alloy containing about 75% palladium and 25% silver.

6. The sensor manufactured by the method as recited in claim 4, wherein said pressure responsive element in the transducer comprises a diaphragm with a plurality of strain responsive element positioned to sense deformation of the diaphragm.

7. The sensor manufactured by the method as recited in claim 4, wherein said pressure transducer further comprises valve means for selectively venting gas from said chamber and said transducer.

8. The sensor manufactured by the method as recited in claim 4, wherein said feedthrough tube is fabricated of nickel.

9. The sensor manufactured by the method as recited in claim 4, further comprising an output tube and wherein said output tube is fabricated of stainless steel.

10. A hydrogen gas sensor for use in an irradiated environment as manufactured by the method as recited in claim 1 comprising: an elongated tube having a wall formed of a palladium silver alloy including 25% silver and an internal chamber which is sealed at one end of the tube, a feedthrough tube having a diameter only slightly greater than the diameter of the elongated tube fabricated of a material which is not permeable to hydrogen gas connected at one end to the other end of the elongated tube and adapted to pass through an opening in a wall, an output tube connected to the other end of the feedthrough tube in axial alignment with the elongated tube and the feedthrough tube, and a pressure transducer connected to the output tube in communication with the chamber in the elongated tube.

11. The sensor of claim 10 wherein the elongated tube has an outer diameter on the order of 1/16 inch and the feedthrough tube as an outer diameter on the order of ¼ inch.

12. The sensor of claim 10 wherein the feedthrough tube is fabricated of nickel.

13. The sensor of claim 10 wherein the output tube is fabricated of stainless steel.

14. The sensor of claim 10 wherein the pressure transducer includes valve means for selectively venting gas from the chamber and the transducer.

* * * * *